United States Patent [19]
Peterson et al.

[11] Patent Number: 5,776,915
[45] Date of Patent: Jul. 7, 1998

[54] PHOSPHOCHOLINES OF RETINOIDS

[75] Inventors: Andrew C. Peterson, Madison, Wis.; Haridasan K. Nair, Williamsville, N.Y.

[73] Assignee: Clarion Pharmaceuticals Inc., Madison, Wis.

[21] Appl. No.: 910,191

[22] Filed: Aug. 12, 1997

[51] Int. Cl.$^6$ .................. A61K 31/685; A61K 9/127; C07F 9/10; C07F 9/09

[52] U.S. Cl. .................. 514/77; 424/450; 554/84; 558/166

[58] Field of Search .................. 514/77; 554/84; 558/166; 424/450

[56] References Cited

U.S. PATENT DOCUMENTS 4,882,165  11/1989  Hunt et al. .................. 424/450
5,489,611   2/1996  Lee et al. .

OTHER PUBLICATIONS

J.P. Frot–Coutaz and L. M. De Luca (1976), *Biochem. J.* 159: 799–801.
M. Karnal et al. (1995), *Bioorg. Med. Chem. Lett.* 5(21): 2461–2464.
P.V. Bhat et al. (1980), *Analytical Biochemistry* 102: 243–248.
K. Tsukida et al. (1982), *J. Nutr. Sci. Vitaminol.* 28: 93–103.
A.Y. Veinberg et al. (1977), *J. Org. Chem. USSR* (Engl. Trans.) 1110–1111 (original Russian–language citation: *Zhurnal Obshchei Khimii* (May 1977) 47(5): 1205–1206).
D.J. Buckner et al. (1991), *FASEB J.* 5: 320–323.
C. Pidgeon and C.A. Munt (1983), *Photochemistry and Photobiology* 37: 491–494.
C.C. Geilen et al. (1992), *Journal of Labelled Compounds and Radiopharmaceuticals* 31(12): 1071–1076.
S.L. Kunkel, "Inflammatory Cytokines", pp. 1–15, in Manual of Vascular Mediators, P.A. Ward, Editor, produced by the publishers of Hospital Practice.
Ralph and Nakoinz, (1977), *J. Immunology* 119: 950–954.
Raschke et al. (1978) *Cell* 15: 261–267.
M.A. Trush et al. (1978), "The Generation of Chemiluminescence by Phagocytic Cells." *Methods in Enzymology* 57:462–494.
"Pharmacological Methods in the Control of Inflammation," Joseph Y. Chang and Alan J. Lewis (eds.), Alan R. Liss, Inc. New York, pp. 221–223 (1989).
S.H. Yuspa et al., *Cancer Research*, 40, 4694–4703, Dec., 1980.

Primary Examiner—Michael G. Ambrose
Attorney, Agent, or Firm—DeWitt Ross & Stevens S.C.; Salvatore R. Conte, Esq.

[57] ABSTRACT

Novel retinoid phosphocholines are disclosed having the general Formula (I):

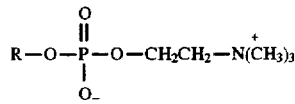

wherein R represents a retinyl or retinoyl moiety. The optical and geometric isomers of compounds of Formula (I) and the pharmaceutically-acceptable salts thereof, are also disclosed. The subject compounds exhibit anti-tumor, anti-psoriatic and anti-inflammatory activities in addition to their inherent Vitamin A-like activities. The invention embraces the novel compounds, pharmaceutical compositions thereof, and methods of using the same.

19 Claims, No Drawings

PHOSPHOCHOLINES OF RETINOIDS

The present invention relates to certain novel phosphocholine derivatives of retinoids, also known as Vitamin A-type compounds, useful as anti-inflammatory, antitumor and anti-psoriatic agents, in addition to the art-recognized therapeutic activities attributed to such retinoids, and pharmaceutical compositions containing such compounds.

DESCRIPTION OF THE PRIOR ART

All of the references cited below are incorporated herein by reference in their entireties.

The term "retinoid(s)" is well understood in the art, as are the related terms "retinyl(s)", "retinoyl(s)" and "retinol(s)". A review of the chemistry and physical properties of natural and synthetic retinoids is found in F. Frickel, "The Retinoids," Vol. I, Academic Press: 1984, pp. 7-145. The synthesis of retinoids is also discussed at length in Sporn, Roberts and Goodman, "The Retinoids: Biology, Chemistry, and Medicine," 2nd ed., Raven Press, Ltd: New York, 1994.

A variety of retinyl- and retinoyl-phosphates and phosphate derivatives, as well as methods for their preparation, are known. A chemical synthesis of all-trans-β-retinoyl phosphate is described in J. P. Frot-Coutaz and L. M. De Luca (1976), *Biochem. J.* 159: 799–801. The synthesis of phosphonate analogs of retinyl phosphate is described in M. Karnal et al. (1995), *Bioorg. Med. Chem. Lett.* 5(21): 2461–2464, in P. V. Bhat et al. (1980), *Analytical Biochemistry* 102: 243–248 and in K. Tsukida et al. (1982), *J. Nutr. Sci. Vitaminol.* 28: 93–103. The Tsukida et al. reference also describes an investigation of the trans-cis stereoisomerism of retinylphosphate and various salts thereof.

The preparation of glycosyl conjugates of retinoids has also been described. The synthesis of sodium retinyl mannosyl phosphate is described in A. Y. Veinberg et al. (1977), *J. Org. Chem. USSR* (Engl. Trans.) 1110–1111 (original Russian-language citation: *Zhurnal Obshchei Khimii* (May 1977) 47(5): 1205–1206). The activity toward the differentiation of HL-60 cells by nitrogen-containing glycosyl conjugates of retinoic acid and retinol has been described in D. J. Buckner et al. (1991), *FASEB J.* 5: 320–323.

The prior art describes an array of therapeutic uses for retinoids. For example, a method of using retinoids to lower plasma concentrations of lipoprotein (A) is disclosed in U.S. Pat. No. 5,489,611. A general disclosure of water-soluble phosphocholine derivatives of compounds which are medically or pharmaceutically active is described in Honda, T. JP Patent 6917-4H (17 May 1990).

The instant assignee's U.S. patent application Ser. No. 60/009,546 entitled RETINOID GLYCEROL PHOSPHO-LIPID CONJUGATES describes the synthesis and anti-psoriatic, anti-inflammatory, and anti-tumor activity of retinoylglycerophosphocholines. A prior reference (C. Pidgeon and C. A. Munt (1983), *Photochemistry and Photobiology* 37: 491–494) describes the synthesis and liposomal properties of 1,2-diretinoyl-sn-glycero-3-phosphocholine and 1-palmitoyl-2retinoyl-sn-glycero-3-phosphocholine, wherein the retinoid moiety of such retinoylglycerophosphocholines is attached to the glycerol backbone by means of a carboxylic acid ester linkage. In contrast, the retinoid moiety contained in the compounds of this invention is bonded to the phosphocholine group via a phosphate linkage.

SUMMARY OF THE INVENTION

The novel phosphocholine conjugates of retinoids and pharmaceutical compositions thereof having the novel anti-inflammatory, anti-tumor and anti-psoriatic utilities of the instant invention in addition to their inherent Vitamin A-like activities, are represented by the general formula:

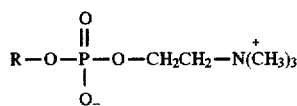

wherein R represents a retinoid moiety, preferably a retinyl or retinoyl moiety. The retinyl and retinoyl moieties are derived from retinoids, those natural or synthetic molecules which exhibit vitamin A-like activity including effects on acne, aging, dry eye, vision, growth, embryonic development, spermatogenesis, regulation of plasma cholesterol or high density lipoprotein or low density lipoprotein levels, female reproduction and regulation of cell differentiation in epithelium, bone, lymphocytes, and hematopoietic, skin and nerve tissue. These retinoids are a family of molecules which exert many of their effects by controlling gene expression through action on a family of nuclear receptors, RAR and RXR receptors, which are members of the steroid receptor super family. Retinol is a natural retinoid alcohol known as "Vitamin A", and retinoic acid is a natural retinoid carboxylic acid that is also known as "Vitamin A acid". The retinoids of the present invention preferably contain either a terminal hydroxy function or a terminal carboxylic acid function.

The retinoid moiety R represents either the retinyl function derived from the corresponding retinoid alcohol or retinol, natural or synthetic, or the retinoyl ester function derived from the corresponding retinoid acid, retinoic acid, natural or synthetic. It also includes any geometric isomer of the retinyl or retinoyl moiety, including all-trans and analogous cis-trans isomers. For example, the retinyl moiety derived from all-trans-retinol has the formula:

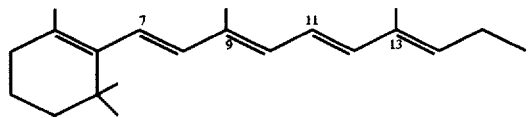

Typical retinol moieties are all-trans-retinol, 9-cis-retinol, 13-cis-retinol and the like.

A further example, the retinoyl ester function derived from all-trans-retinoic acid has the formula:

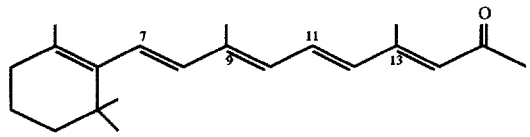

Typical retinoyl ester moieties are all-trans-retinoyl, 9-cis-retinoyl, 13-cis-retinoyl and the like.

The most preferred compounds of Formula (I) are all-trans-retinylphosphocholine and all-trans-retinoylphosphocholine.

Other particular compounds of Formula (I) are: 13-cis-retinylphosphocholine, 9-cis-retinylphosphocholine, 9-cis-retinoylphosphocholine and 13-cis-retinoylphosphocholine.

The compounds of Formula (I) may exist in isomeric forms within the retinoid moiety R. For example, the compounds of Formula (I), may have an asymmetric carbon within R and, consequently, they can exist in the form of different combinations of R and S isomeric forms as enantiomers, diastereomers or racemates.

In addition cis- and trans-geometric isomers may also be present in the subject compounds within R due to the cis- and trans-configuration inherent with the double bonds. Thus, by initially starting with an appropriate cis- or trans-precursor, the corresponding end product of Formula (I) will be obtained.

All racemic and isomeric forms of the compounds of Formula (I), including pure enantiomeric, diastereomeric and geometric isomers and mixtures thereof, are intended to be within the scope of this invention. Unless otherwise specified, the compounds of the hereinafter examples are in achiral or racemic form.

The invention also comprehends salts of the Formula (1) compounds. Such salts include acid addition salts such as, for example, those made from inorganic acids such as hydrochloric, nitric, and the like acids or from organic acids such as citric, lactic and the like organic acids. The salts also include these made with bases such as, for example sodium and potassium hydroxide. The salts of the invention are made by conventional methods well known to those skilled in the art. The salts for therapeutic use of the Formula (I) compounds are pharmaceutically-acceptable salts, as well understood in the art.

It has now been found that the Formula (I) compounds, including pharmacologically active isomers and pharmaceutically-acceptable salts thereof, possess anti-inflammatory, anti-tumor and anti-psoriatic activities. Accordingly, they are useful, respectively, in the treatment of disease conditions wherein inflammation is a contributing factor, in the treatment of tumors, particularly solid tumors, and in the treatment of psoriasis.

In addition, retinol, retinoic acid and related retinoids are poorly soluble in water, whereas the phosphocholines of Formula (I) are readily soluble in water. This enhanced water solubility improves the ease of formulation in aqueous solutions and other preparations. The phosphocholines of Formula (I) also retain their lipid solubility properties. This amphoterism generally assists in the pharmaceutical formulation of the Formula (I) compounds for both systemic and topical applications. Since skin and tissues are comprised of phospholipids related to the Formula (I) compounds, the Formula (I) compounds are able to penetrate tissues and skin readily, making them particularly suitable for topical applications.

The invention thus provides a method of treating a host mammal afflicted with an inflammatory disorder comprising administering to said mammal an effective anti-inflammatory amount of a compound of Formula (I) or a pharmaceutically-acceptable salt thereof and a pharmaceutically-acceptable carrier. A further aspect of the invention provides a method of treating a host mammal afflicted with tumors comprising administering to said mammal an effective anti-tumor amount of a compound of Formula (I) or a pharmaceutically-acceptable salt thereof and a pharmaceutically-acceptable carrier. Another aspect of the invention provides a method of treating a host mammal afflicted with psoriasis with an effective anti- psoriatic amount of Formula (I) or a pharmaceutically-acceptable salt thereof and a pharmaceutically-acceptable carrier. Still another aspect of the invention provides a method of topical treatment of a host mammal with an effective anti-psoriatic or anti- inflammatory amount of a water soluble and dermal-penetrating compound of Formula (I) or a pharmaceutically-acceptable salt thereof and a pharmaceutically-acceptable carrier.

CHEMISTRY

The compounds of Formula (1) are prepared by the synthetic procedures outlined in the following Reaction Schemes and subsequent examples. Working up of the individual stepwise products in the synthetic procedures may be advantageously carried out if necessary by standard methodologies, for example, by evaporating down the reaction solution or precipitating the particular product from the reaction solution by dilution with an appropriate antisolvent. The intermediate products obtained may be quite suitable without further purification operations for the preparation of the final products, which then may be purified. Purification is readily achieved by conventional methods in the art, for example, by recrystallization techniques, chromatography and the like.

REACTION SCHEME

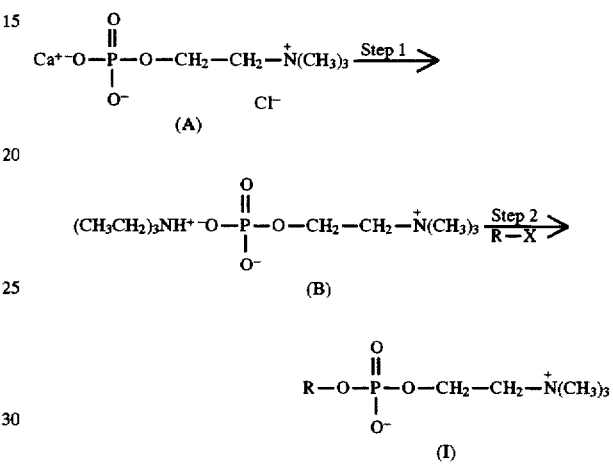

Step 1:

The triethylammonium salt of phosphoryl chorine (B) is prepared by the analogous method used to prepare the tetra-n-butylammonium salt of phosphoryl chorine which is described in C. C. Geilen et al. (1992), *Journal of Labelled Compounds and Radiopharmaceuticals* 31(12): 1071–1076. The commercially available calcium tetrahydrate salt of phosphorylcholine chloride (A) is treated with a solution of oxalic acid in water. The calcium oxalate which precipitates is filtered off and the filtrate is treated with triethylamine to yield the triethylammonium salt of phosphoryl choline which is obtained after concentration of the filtrate.

Step 2:

In Step 2, R—X represents the retinoid reactant, wherein X represents the reacting hydroxyl or carboxyl function. Several of the R—X retinoids are commercially available, such as all-trans-retinol, 13-cis-retinol, all-trans-retinoic acid, 9-cis-retinoic acid and 13-cis-retinoic acid. Other retinoids of formula R—X are known in the literature or are obtainable by art-recognized procedures.

The indicated phosphoethanolamine moiety is introduced by reaction of the hydroxyl or carboxylic acid function in the retinoid R—X with trichloroacetonitrile and triethylammonium phosphorylcholine (B), in a polar, aprotic solvent, preferably acetonitrile, to yield Compound (I) by the analogous method described in K. Tsukida and K. Saiki (1982), *J. Nutr. Sci. Vitaminol* 28: 93–103 and J. P. Frot-Coutaz and L. M. DeLuca (1977), *Biochem J.* 159:799–801.

UTILITY

The compounds of Formula (I), including the pharmaceutically-acceptable salts and isomeric forms thereof, are useful therapeutic agents for treating inflammation, tumors and psoriasis in mammals, including humans.

1. ANTI-INFLAMMATORY

Inflammation is a complex process, involving a variety of cell types including macrophages, for example, see S. L. Kunkel, "Inflammatory Cytokines", pp. 1–15, in "Manual of Vascular Mediators," P. A. Ward, Editor, produced by the publishers of Hospital Practice. References relative to macrophages are numerous, including, for example, Ralph and Nakoinz, (1977), *J. Immunology* 119: 950–954, and Raschke et al. (1978) Cell 15: 261–267.

The anti-inflammatory activity of the herein-described compounds of Formula (I) and pharmaceutically-acceptable salts thereof may be assayed by methodologies conventional in the art, such as the following:

A. In Vitro Assay: Assay for Anti-inflammatory Activity by Inhibition of Macrophage Macrophages are activated by infection and by a wide variety of non-infectious irritants and pro-inflammatory agents. Upon activation, macrophages participate in a variety of reactions. They may phagocytize bacteria and kill them by either oxygen-dependent or oxygen-independent pathways. With respect to the oxygen-dependent pathways, activation of macrophages induces them to increase oxygen consumption and produce reactive oxygen species (for example, radicals such as superoxide). Production of reactive oxygen species by activated macrophages is associated with inflammatory responses. In addition, on activation, macrophages release a variety of inflammatory cytokines, including several interleukins and tumor necrosis factor α(TNF-α). Inhibition of any of these activation-related processes can lead to reduced inflammation.

For these reasons, macrophage activation is of critical importance in studies of the inflammatory process. Agents that reduce macrophage activation are likely to have utility as anti-inflammatory agents.

The RAW 264.7 cell line (available from the American Type Culture Collection under Accession No. TIB 71) is a murine monocyte/macrophage line, the cells of which show many of the differentiative functions of a macrophage. Like macrophages, the cells are capable of phagocytosis and undergo an oxidative burst (increased oxygen consumption) and production of oxygen radicals (e.g., superoxide) in response to appropriate signals. Agents that inhibit the activation of these cells in vitro, so as to inhibit the respiratory burst and corresponding production of oxygen radicals associated with the activation, are therefore inhibitors of macrophage activation and critical steps in inflammatory processes.

The respiratory burst and corresponding production of oxygen radicals that accompany macrophage activation can be measured in a variety of ways, including chemiluminescence based on the reaction of the oxygen radicals with luminol added to the culture medium (see M. A. Trush et al. (1978), "The Generation of Chemiluminescence by Phagocytic Cells," *Methods in Enzymology* 57:462–494). Indeed, chemiluminescence generated from luminol in the culture medium of macrophage cell lines is recognized in the art as a marker of macrophage activation.

1. Cell line: Raw 264.7 (ATCC TIB-71, attachment dependent);
2. Culture medium: Dulbecco's Modified Eagle's Medium (DMEM, Sigma Chemical Co. Cat. No. D-7777) with 10% Fetal Bovine Serum (FBS);
3. Standard protocol for culturing cell lines: in T-75 or T-150 flasks; 37° C.; 95% air, 5% $CO_2$; 100% humidity;
   a. Cell line is passaged when approximately 80% confluent; with trypsin (1 mg/mL) and ethylenediamine tetraacetic acid (EDTA) (1 µM in Ca—Mg free Hank's balanced salt solution); at a 1:4 to 1:5 spilt;
   b. All procedures are performed aseptically in a class II biological safety cabinet using standard Biosafety Level 2 (BL-2) containment procedures. In order to prevent genetic drift in stock cell lines, fresh cultures are prepared at approximately monthly intervals with cells thawed from liquid nitrogen storage.
4. Methodology:
   a. After cell passage, count cells with a hemacytometer;
   b. Adjust cell concentration to approximately 1,000,000 cells per mL;
   c. Suspend cells in DMEM lacking phenol red and without FBS;
   d. Pipette 1 mL of cell suspension into a standard luminometer cuvette (12×75), commercially obtainable from Analytical Luminescence Laboratories, San Diego, Calif., USA;
   e. Add luminol to final concentration of 0.2 µM;
   f. Add test compound dissolved in phosphate buffered saline (PBS), or in dimethyl sulfoxide (DMSO) for the comparative compound, all-trans-retinoic acid, for final concentration levels ranging from 0 to 30 µM;
   g. Add 100 nanograms of phorbol myristate acetate (PMA); and
   h. Wait 1 minute and read photo counts (i.e., luminescence) on a Monolight 2010 luminometer available from Analytical Luminescence Laboratories, San Diego.
5. Data Analysis:

Background-no test compound present; no PMA present;
   Control-no test compound present;
   Calculate:

% Inhibition=1−{L(test compound)−L(background)/(L(control)−L(background)}×100 where L is luminescence.
6. Results indicate the marked inhibition of luminescence by the Formula (1) compounds.

B. In Vivo Assay: Mouse Ear Inflammation Model

A common in vivo model for the evaluation of anti-inflammatory agents is phorbol myristate acetate (PMA)-induced inflammation in mouse ears. This method is described in "Pharmacological Methods in the Control of Inflammation," Joseph Y. Chang and Alan J. Lewis (eds.), Alan R. Liss, Inc. New York, pp. 221–223 (1989). In this assay, edema, which is characteristic of inflammation, is quantified by determining ear thickness or ear weight approximately 6 hours after applying PMA to the ear.

1. Mice: Male CD-1, 21–24 g (Product Number 3002) obtainable from Harlan Sprague, Dawley, Indianapolis, Ind., USA.
2. Methodology:
   a. Prepare 0.01% (w/v) PMA in a mixture of equal volumes of acetone and ethanol and further containing 0 (vehicle), 1%, 2.5%, and 5% (w/v) of the test compound;
   b. Prepare vehicle control solution of equal volumes of acetone and ethanol;
   c. Prepare control solution of 0.01% (w/v) PMA in a mixture of equal volumes of acetone and ethanol, containing 1% dexamethasone;
   d. Divide mice into groups of 3;
   e. Treat each group of mice by applying 20 µL of one of the above solutions to the right ear using a micropipetter;
   f. Wait 6 hours and euthanize the mice in a $CO_2$ chamber;
   g. Cut the ears and punch out circles of 6-mm diameter;
   h. Measure the weight of three appropriate ear punches in the same group together;

i. Determine the average weight of all untreated ear samples (average weight of control ear);

j. Determine the average weight of each group of test ear samples (average weight of test ear);

k. Calculate average % increase in ear weight as follows:

Average % increase in ear weight={(Average weight of test ear)−(Average weight of control ear)/(Average weight of control ear)}×100

3. Results:

The positive results obtained in the foregoing assays are illustrative of the anti-inflammatory activity of the Formula (I) compounds. These compounds thus have utility in treating those disease states where inflammation is a contributing or major factor, such as in bronchial asthma, rheumatoid arthritis, osteoarthritis, psoriasis, and immediate and delayed-type hypersensitivity reactions.

The instant invention thus provides a method of treating inflammation in a mammal afflicted with same comprising administering to said mammal an effective antiinflammatory amount of a compound of Formula (I) or a pharmaceutically-acceptable salt thereof. It also provides pharmaceutical composition an effective antiinflammatory amount of a compound of Formula (I) or a pharmaceutically-acceptable salt thereof and a pharmaceutically-acceptable carrier.

II. ANTI-TUMOR:

The following testing procedure, using the identified promyelocytic leukemic HL60 cell line and the human breast and human colon carcinoma cell lines in an in vitro assay, demonstrates the marked anti-tumor (or antineoplastic) activity of the subject compounds.

1. Human tumor cell line, obtainable from the American Type Culture Collection (ATCC): HL-60 (ATCC HTB-240): a promyelocytic leukemic cell line.

2. Culture media: Roswell Park Memorial Institute-1640 (RPMI-1640) plus 10% Fetal Bovine Serum (FBS).

3. Standard protocol for culturing cell lines: in T-75 or T-15 flasks; 37° C.; 95% air, 5% $CO_2$; 100% humidity.

a. The HL-60 cell line is passaged by removing approximately 75% of the media and cell mixture and adding an equal amount of fresh media once or twice a week.

b. All procedures are performed aseptically in a Class II biological safety cabinet using standard BL-2 containment procedures. At approximately monthly intervals, fresh cells are thawed from liquid nitrogen storage in order to prevent genetic drift in stock cell lines.

4. Methodology a. After cell passage, count cells with a hemacytometer;

b. Adjust cell concentration to approximately 20,000 cells per 100 μL;

c. Pipette 100 μL cell suspension into each well of a standard 96-well microtiter plate.

d. Add test compound dissolved in phosphate buffered saline (PBS), or in DMSO for the comparative compound, retinoic acid, for final concentration levels ranging from 0 to 100 μM;

e. Adjust volume to 200 μL per well by adding Roswell Park Memorial Institute-1640 (RPMI-1640, Sigma Chemical Co. Cat. No. R-6504); and f. Incubate 72 hours under standard culture conditions and determine end points.

5. End Point 1: Cell Proliferation a. Add 100 μL per well of cold (4° C.) 50% (w/v) trichloroacetic acid (TCA) in water;

b. Do not move the plate for 5 minutes;

c. Place the plate at 4° C. for one hour;

d. Remove TCA and rinse cells 5 times with tap water;

e. Air-dry plates;

f. Add 50 μL/well of 0.4% (w/v) sulforhodamine B (SRB) in 1% (v/v) acetic acid in water;

g. After 30 minutes at room temperature, rinse cells 4 times with 1% (v/v) acetic acid in water to remove residual stain;

h. Air-dry plates;

i. Dissolve stain by adding 100 μL/well of unbuffered Tris base. pH 10.5; and j. Read absorbance at 562 nm using a standard 96-well microtiter plate reader. Absorbance readings are linear with dye concentrations below 1.8 absorbance units. To reduce absorbance, decrease wavelength at which measurements are taken.

k. Data Analysis: single point reading: the higher the absorbance, the higher the cell number;

control-no test compound present in culture medium;

background-no cell and no test compound present in the culture medium;

initial control cell number (ICCN)-no test compound present in culture medium, end point is determined at time of treatment;

final control cell number (FCCN)-no test compound present in culture medium, end point determined at 72 hours after treatment;

final cell number (FCN)-test compound present in culture medium, end point determined at 72 hours after treatment;

calculate:

ICCN=A(control, zero hour)−A(background)

FCCN=A(control, 72 hours)−A(background)

FCN=A(test compound, 72 hours)−A(background)

% Relative Increase in Cell Number=FCN-ICCN/FCCN-ICCN× 100 where A is absorbance.

6. Results:

The positive results obtained in the foregoing assay are illustrative of the anti-tumor or anti-cancer activity of the Formula (I) compounds, particularly against human myelocytic leukemia. Anti-tumor activity is to be expected against a wide spectrum of mammalian (including human) tumors and cancerous growths.

The instant invention thus provides a method of treating tumors in a mammal afflicted with same comprising administering to said mammal an effective anti-tumor amount of a compound of Formula (I) or a pharmaceutically-acceptable salt thereof. It also provides pharmaceutical compositions comprising an effective anti-tumor amount of a compound of Formula (I) or a pharmaceutically-acceptable salt thereof and a pharmaceutically-acceptable carrier.

III. ANTI-PSORIATIC

Psoriasis is a chronic inflammatory dermatosis characterized, in part, by hyperproliferation of keratinocytes and release of pro-inflammatory cytokines. Compounds that reduce hyperproliferation of keratinocytes in vitro are likely to have utility in the control of psoriasis. As will be shown, using the assay described below, the compounds of Formula (1) markedly inhibit the proliferation of these cells in vitro, thus indicating that these compounds are useful in ameliorating psoriasis.

Assay for the anti-psoriatic activity by inhibition of kerotinocyte proliferation:
1. Cell line: PAM-212 murine kerotinocyte cell line isolated and cultivated from newborn BALB/C mice (see S. H. Yuspa et al., *Cancer Research*, 40, 4694–4703, December, 1980) that appears to retain many characteristics of normal keratinocytes.
2. Culture medium: 1:1 DMEM and Ham's Nutrient Mixture F-12 (Ham's F-12, Sigma Chemical Co. Cat. No. D-2906) with 10% FBS
3. Culture conditions are the same as those described in part 3 of the assay protocol for anti-tumor activity.
4. Methodology is the same as that described in part 4 of the assay protocol for antitumor activity, except that, with reference to part 4(b) of the assay protocol for antitumor activity, cell concentration in this case is adjusted to 1,000 cells per 100 mL (rather than 20,000 cells per 100 μL).
5. End Point determination and analysis are as described in part 5 of the assay protocol for anti-tumor activity.
6. Results:
   The positive results obtained in the foregoing assay illustrate the anti-psoriatic activity of the Formula (I) compounds. These compounds thus have utility in treating psoriasis.

The instant invention thus provides a method of treating psoriasis in a mammal afflicted with same comprising administering to said mammal an effective anti-psoriatic amount of a compound of Formula (I) or such salt and a pharmaceutically-acceptable carrier. It also provides pharmaceutical compositions comprising an effective anti-psoriatic amount of a compound of Formula (I) or such salt and a pharmaceutical acceptable carrier.

PHARMACEUTICAL COMPOSITIONS

Another aspect of the invention provides pharmaceutical compositions, for medical use, comprising an active compound, i.e., a Formula (I) compound or a pharmaceutically-acceptable salt thereof, together with an acceptable carrier therefor and optionally other therapeutically active ingredients. The carrier must be pharmaceutically-acceptable in the sense of being compatible with the other ingredients of the formulation and not deleterious to the recipient thereof. The compositions include those suitable for oral, topical, inhalation, rectal or parenteral (including subcutaneous, intramuscular and intravenous) administration.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating each of the indicated activities. All methods include the step of bringing the active compound into association with a carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula (1) which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the compounds of Formula (I) are preferable utilized at a concentration of from about 0.1% to 5.0% by weight.

Compositions suitable for rectal administration, preferably for the treatment of hemorrhoids and the like, comprise a suppository, preferably bullet-shaped, containing the active ingredient and pharmaceutically-acceptable vehicles therefore such as hard fat, hydrogenated cocoglyceride, polyethylene glycol and the like. In suppository formulations, the compounds of Formula (1) are preferably utilized at concentrations of from about 0.1% to 10% by weight.

Compositions suitable for rectal administration, preferred for the treatment of ulcerative colitis and the like, also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the compounds of Formula (1) are preferably utilized at concentrations of from about 5.0–10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula (I) are preferable utilized at concentrations of from about 0.1% to 5.0% by weight applied to a dressing.

Compositions suitable for administration by inhalation to treat, for example, acute or chronic bronchial asthma, include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from a conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula (I) required to be effective for each of the indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.5 to about 500 mg/kg body weight per day, preferably in the range of about 5 to about 350 mg/kg per day, calculated as the non-salt form of Formula (I). The total daily dose may be given as a single dose, multiple doses, e.g., two to six times per day, or by intravenous infusion for a selected duration. Dosages above or below the range cited above are within the scope of the present invention and may be administered to the individual patient if desired and necessary. In general, the pharmaceutical compositions of this invention contain from about 0.5 mg to about 15 g and, preferably, from about 7.5 to about 1500 mg per day, and a typical dose would be about 800 mg per day. If discrete multiple doses are indicated, treatment might typically be 100 mg of a compound of Formula (I) given twice per day.

Still another aspect of the present invention comprises the Formula (I) compounds or a pharmaceutically-acceptable salt thereof in the novel physical form of a liposome. Liposomes, which are microscopic, man-made spheres of fatty material, were first formed from phospholipids. Although it has been known for a long time that other lipids, such as cholesterol, dicetyl phosphate, and stearylamine can be incorporated into liposome membranes that contain phospholipids, only phospholipids were known to form such structures when suspended in aqueous media on their own. Subsequently, it was found that certain ammonium salts could also form liposomes. In particular, dialkyl dimethyl ammonium salts will form liposomes if the alkyl chains are 12 carbons or longer. More recently, there have been developed a series of novel structures, based on the chemical structure of phospholipids, that also form liposomes. In addition, much information has been gained on the type of chemical structure necessary for liposome formation. Usually, the molecule must be one with two alkyl chains and a polar headgroup, although there are some exceptions to this rule. For example, fatty acids, which have only a single alkyl chain, will form liposome structures under conditions where hydrogen bonding turns them into dimers.

Superficially, the structure of the Formula (I) compounds does not seem likely for liposome formation. It has only a single alkyl moiety, namely the retinoid group connected to a phosphoryl choline group. Molecules of this type usually form micelles. However, the ability of the Formula (I) compounds to form a liposome can be explained retrospectively by pointing to the bulky nature of the retinoid group, which may make it equivalent in molecular terms to a dialkyl structure containing only straight hydrocarbon chains. One could still not predict from this consideration that this molecule would form a liposome. It might form a number of more complex micellar structures, or might not even suspend at all in aqueous medium. Therefore, the capacity of this compound to form a liposome is a novel observation that could not have been predicted until the observation had been made. It also might have been overlooked had not the temperature been taken sufficiently high to induce swelling of the lipid film, as indicated in Example 7 hereafter, which more fully details the preparation of the subject liposomes.

This novel liposome form of retinoids or a pharmaceutically-acceptable salt thereof has beneficial pharmaceutical applications. For example, it may be incorporated into topical pharmaceutical applications of the subject compounds such as, for example, ointments, salves, creams and creamy liquids, dispersions and the like. The subject liposomes are also suitable for transdermal application of other therapeutic agents by enhancing the absorption of such agents through the skin of humans and animals. As with other known liposomes, such agents would be encapsulated within the internal aqueous compartment of the liposome structure.

In addition to encapsulation of drugs within the internal aqueous space, liposomes may also be prepared from mixtures of subject compounds with other amphophilic therapeutic agents, such as, for example, phospholipids, cholesterol and certain drugs such as amphotericin B, doxorubicin and $1\alpha,25$-dihydroxy Vitamin $D_3$. The preparation strategy would require the mixing of the compound of Formula (I) with the other component in an organic solvent. This initial mixing would then be followed, for example, by evaporation of the solvent to give a mixed film of the components. This film would then be swollen in aqueous medium as described in Example 7.

It is expected that the subject compounds would respond to other techniques known in the art for liposome formation. These include the reverse phase evaporation method, the dehydration-rehydration method, and solvent injection methods. It is also expected that the subject compounds would respond to other size control methods in addition to sonification. Principal among these is the method of extrusion through polycarbonate membranes, or on an industrial scale, filtration with ceramic filters.

The subject invention thus provides a compound of Formula (I) or a pharmaceutically-acceptable salt thereof in the form of a liposome. The invention also provides pharmaceutical compositions comprising said liposome in a pharmaceutically-acceptable carrier, particularly for topical application, as well as such pharmaceutical wherein the liposome comprised of a retinoid-phosphocholine of Formula (I) contains another drug encapsulated within its structure.

The following examples are intended to illustrate and not to limit the scope of the present invention.

EXAMPLE 1
Triethylammonium phosphorylcholine

The phosphorylcholine chloride, calcium salt tetrahydrate (100 g, 0.30 mol) is treated with an aqueous solution of oxalic acid (40.52 g, 0.45 mol) in 800 mL water at room temperature. Calcium oxalate precipitates as a fine white solid. The aqueous solution containing the precipitate is filtered through a bed of celite and washed with 2×200 mL water. The filtrate is treated with triethylamine with vigorous stirring until the pH reaches pH 9. The pH of the filtrate is monitored by use of standard pH paper. The resultant solution is then evaporated to dryness. Toluene (250 mL) is added to the residue, the resultant solution is concentrated to dryness and this process is repeated twice more. The resultant residue is further dried to yield triethylammonium phosphorylcholine as a viscous residue which may be used in the next synthetic step without further purification.

EXAMPLE 2
all-trans-Retinylphosphocholine

Trichloroacetonitrile (25 mL) is added to a solution of all-trans-retinol (1.0 g, 3.49 mmol) in acetonitrile (50 mL) under nitrogen cooled with an ice-water bath and protected from light. A solution of triethylammonium phosphorylcholine (1.84 g, 6.65 mmol) in acetonitrile (200 mL) is then added over a 30 minute period at room temperature. The resultant reaction mixture is heated to 45° C. for 2 hours and then is cooled to 0°–4° C. with an ice water bath. Concentrated aqueous $NH_4OH$ (1.5 mL) is added to the cooled reaction mixture over a 15 minute period. The resultant solution is concentrated in vacuo. The residue is dissolved in 2-propanol (5 mL) and all-trans-retinylphosphocholine is precipitated upon addition of acetone (200 mL) at 0° C. The product is purified by recrystallization from 2-propanol-acetone and is dried in vacuo to yield all-trans-retinylphosphocholine as a pale yellow powder.

EXAMPLE 3

By following the procedure outlined in Example 2, except that an equivalent amount of the appropriate R—X is employed as the starting material, the following representative compounds of Formula (I) are obtained: 9-cis-retinylphosphocholine and 13-cis-retinylphosphocholine.

EXAMPLE 4
all-trans-Retinoylphosphocholine

A solution of trichloroacetonitrile (50 mL) and triethylammonium phosphorylcholine (4.98 g, 17.5 mmol) in acetonitrile (500 mL) is added to a solution of all-trans-retinoic acid (2.1 g, 6.99 mmol) in acetonitrile (500 mL), which is protected from light, at room temperature under nitrogen. The resultant mixture is stirred at room temperature under nitrogen for 8 hours. The reaction mixture is cooled to 0° C. and is neutralized by addition of concentrated aqueous $NH_4OH$ (3 mL) over a 30 minute period. The resultant mixture is concentrated in vacuo and purified to yield all-trans-retinoylphosphocholine as a yellow powder by column chromatography followed by drying in vacuo.

EXAMPLE 5

By following the procedure outlined in Example 1, except that an equivalent amount of the appropriate R—X is employed as the starting material, the following representative compounds of Formula (I) are obtained: 9-cis-retinoylphosphocholine and 13-cis-retinoylphosphocholine.

EXAMPLE 6

Unless otherwise specified, the term "Active Ingredient" denotes one of the herein described compounds of the subject invention.

A. This is an illustrative example of tablets containing the following ingredients which may be prepared in a conventional manner

| Ingredient | Per Tablet (mg) |
|---|---|
| Active Ingredient | 5–20 |
| Lactose | 70 |
| Maize starch | 70 |
| Polyvinylpyrrolidine | 5 |
| Magnesium Stearate | 5 |
| Tablet weight | 155-170 |

B. An illustrative oil-in-water cream base formulation can be prepared for topical use from the following ingredients

| Ingredient | Grams |
|---|---|
| all-trans-Retinoylphosphocholine | 1.0 |
| Anhydrous lanolin | 20.0 |
| Polysorbate | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water, to | 100.0 |

C. An illustrative inhalation cartridge formulation for administration by inhalation

| Ingredient | Amount per Cartridge |
|---|---|
| Active Ingredient, (10–50 microns) | 5.0 mg |
| Lactose q.s. | 25.0 mg |

The active ingredient, premicronized to a fine particle size 1–50 μm in diameter, is blended with normal tabletting grade lactose in a high energy mixer. The powder blend is filled into appropriately sized hard gelatin capsules on a suitable encapsulation machine. The contents of the cartridges are administered using an appropriate powder inhaler.

D. An illustrative pharmaceutical composition for parenteral or intravenous administration can be prepared from the following ingredients with appropriate sterilization

| Ingredient | Amount per ampoule |
|---|---|
| all-trans-Retinylphosphocholine | 50 mg |
| Buffering Agent | q. s. |
| Saline | 1 mL |

E. An illustrative rectal enema formulation for administration by a suppository containing the following ingredients which may be prepared in a conventional manner

| Ingredient | Amount per suppository |
|---|---|
| 9-cis-Retinoylphosphocholine | 500 mg |
| Hydrogenated Cocoglyceride | 5 g |

The active ingredient and pharmaceutically-acceptable vehicle are thoroughly mixed and shaped into an appropriate form.

F. An illustrative rectal enema formulation for administration by a rectal enema unit containing the following ingredients which may be prepared in a conventional manner

| Ingredient | Amount per rectal enema unit |
|---|---|
| Active Ingredient | 4 g |
| Buffering Agent | q. s. |
| Saline | 60 mL |

The active ingredient and buffering agents are dissolved in the saline solution. The resultant solution is filtered and is filled into a rectal enema unit.

G. An illustrative example of capsules containing the following ingredients which may be prepared in a conventional manner

| Ingredient | Per Capsule (mg) |
|---|---|
| Active Ingredient | 50 |
| Lactose | 450 |
| Magnesium Stearate | 5 |
| Capsule weight | 505 |

H. An illustrative example of water-soluble gels containing the following ingredients which may be prepared in a conventional manner

| Ingredient | Per Packet (mg) |
|---|---|
| 13-cis-Retinoylphosphocholine | 195 |
| Carbomer 934P | 400 |
| Propylene glycol | 400 |
| Purified water, to | 2900 |
| Package weight | 3895 |

I. An illustrative example of water-insoluble ointments containing the following ingredients which may be prepared in a conventional manner

| Ingredient | Per Tube (g) |
|---|---|
| Active Ingredient | 1.0 |
| Lactose | 2.0 |
| Mineral Oil | 11.0 |
| Polyethylene | 6.0 |
| Tube weight | 20.0 |

J. An illustrative example of lotions containing the following ingredients which may be prepared in a conventional manner

| Ingredient | Per Bottle |
|---|---|
| Active Ingredient | 1.425 mg |
| Cetyl Alcohol | 2 mL |
| Steric Acid | 2 mL |
| Glycerin | 15 mL |
| Triethanolamine | 4 mL |
| Purified Water, to | 24 mL |
| Bottle volume | 57 mL |

EXAMPLE 7

A. Five micromoles of a compound of Formula (I) are dissolved in about 1 mL of chloroform. The solution is transferred to a 16×120 mm screw-capped tube. The tube is placed, uncapped, inside a 1×8 inch boiling tube with a B24/40 standard glass fitting. Inside the boiling tube, in the space between the boiling tube and the smaller screw-capped tube, there is a small amount of distilled water to aid thermal contact between the inner and outer tubes. The boiling tube is placed on a rotary evaporator under reduced pressure to evaporate the chloroform and leave the lipid as a thin film in the lower portion of the screw-capped tube. The boiling tube is partly immersed in a water bath at 37° C. during the evaporation to aid the process.

Once a thin film has been formed, the screw-capped tube is removed from the boiling tube, and 1 mL of aqueous solution is added to it. The tube is capped and immersed in a water bath at 75° C. to aid swelling of the lipid. Swelling of the film is observed to occur when the film becomes cloudy, and is, with agitation, dislodged from the walls of the tube to give a cloudy suspension in the aqueous medium. This suspension is found to consist of liposomes by the application of two techniques. First, laser-light scattering, or QELS, reveal the presence of particles of 400–1800 nm in diameter. Second, electron microscopy shows that these particles have the characteristic concentric lamellar structure of liposomes.

B. Liposomes of the iodide salt of a compound of Formula (I) are obtained by following the foregoing procedures.

It is understood that the invention is not limited to the compounds, compositions, methods, reagents and reactions described in the foregoing examples, but encompasses all modifications thereof as are encompassed by the following claims.

We claim:

1. A retinyl- or retinoylphosphocholine selected from the group consisting of Formula (I) compounds:

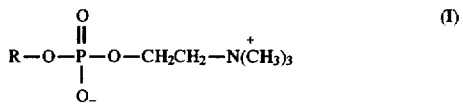

wherein R represents a retinyl or retinoyl moiety, and pharmaceutically-acceptable salts thereof.

2. The phosphocholine of claim 1 which is all-trans-retinylphosphocholine or all-trans-retinoylphosphocholine.

3. The phosphocholine of claim 1 which is 9-cis-retinylphosphocholine, 13-cis-retinylphosphocholine, 9-cis-retinoylphosphocholine, or 13-cis-retinoylphosphocholine.

4. A method of treating inflammation, tumors, or psoriasis in a mammal which comprises administering to the mammal an effective anti-inflammatory, anti-tumor or anti-psoriatic amount, respectively, of one or more retinyl- or retinoylphosphocholines selected from the group consisting of formula (I) compounds:

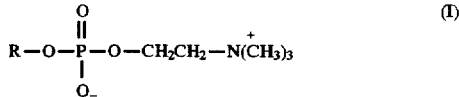

wherein R represents a retinyl moiety, and pharmaceutically-acceptable salts thereof.

5. The method of claim 4 wherein a Formula I compound selected from the group consisting of all-trans-retinylphosphocholine, all-trans-retinoylphosphocholine, and combinations thereof, is administered to the mammal.

6. The method of claim 4 wherein a Formula I compound selected from the group consisting of 9-cis-retinylphosphocholine, 13cis-retinylphosphocholine, 9-cis-retinoylphosphocholine, 13cis-retinoylphosphocholine, and combinations thereof, is administered to the mammal.

7. A method of treating inflammation in a mammal which comprises administering to the mammal an effective anti-inflammatory amount of one or more retinyl- or retinoylphosphocholines selected from the group consisting of Formula (I) compounds:

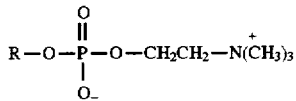
(I)

wherein R represents a retinyl or retinoyl moiety, and pharmaceutically-acceptable salts thereof.

8. The method of claim 7 wherein a Formula I compound selected from the group consisting of all-trans-retinylphosphocholine, all-trans-retinoylphosphocholine, and combinations thereof, is administered to the mammal.

9. The method of claim 7 wherein a Formula I compound selected from the group consisting of 9-cis-retinylphosphocholine, 13-cis-retinylphosphocholine, 9-cis-retinoylphosphocholine, 13-cis-retinoylphosphocholine, and combinations thereof, is administered to the mammal.

10. A method of treating a tumor in a mammal which comprises administering to the mammal an effective anti-tumor amount of one or more retinyl- or retinoylphosphocholines selected from the group consisting of Formula (I) compounds:

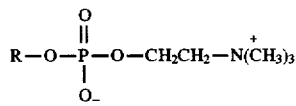
(I)

wherein R represents a retinyl or retinoyl moiety, and pharmaceutically-acceptable salts thereof.

11. The method of claim 10 wherein a Formula I compound selected from the group consisting of all-trans-retinylphosphocholine, all-trans-retinoylphosphocholine, and combinations thereof, is administered to the mammal.

12. The method of claim 10 wherein a Formula I compound selected from the group consisting of 9-cis-retinylphosphocholine, 13-cis-retinylphosphocholine, 9-cis-retinoylphosphocholine, 13-cis-retinoylphosphocholine, and combinations thereof, is administered to the mammal.

13. A method of treating psoriasis in a mammal which comprises administering to the mammal an effective anti-psoriatic amount of one or more retinyl- or retinoylphosphocholines selected from the group consisting of Formula (I) compounds:

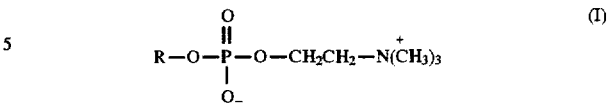
(I)

wherein R represents a retinyl or retinoyl moiety, and pharmaceutically-acceptable salts thereof.

14. The method of claim 13 wherein a Formula I compound selected from the group consisting of all-trans-retinylphosphocholine, all-trans-retinoylphosphocholine, and combinations thereof, is administered to the mammal.

15. The method of claim 13 wherein a Formula I compound selected from the group consisting of 9-cis-retinylphosphocholine, 13-cis-retinylphosphocholine, 9-cis-retinoylphosphocholine, 13-cis-retinoylphosphocholine, and combinations thereof, is administered to the mammal.

16. A pharmaceutical composition comprising an effective anti-inflammatory, anti-tumor, or anti-psoriatic amount of one or more retinyl- or retinoylphosphocholines selected from the group consisting of Formula (I) compounds:

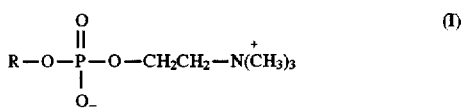
(I)

wherein R represents a retinyl or retinoyl moiety, and pharmaceutically-acceptable salts thereof.

17. The pharmaceutical composition of claim 16 wherein the Formula I compound is selected from the group consisting of all-trans-retinylphosphocholine, all-trans-retinoylphosphocholine, and combinations thereof.

18. The pharmaceutical composition of claim 16 wherein the Formula I compound is selected from the group consisting of 9-cis-retinylphosphocholine, 13-cis-retinylphosphocholine, 9-cis-retinoylphosphocholine, 13-cis-retinoylphosphocholine, and combinations thereof.

19. A retinyl- or retinoylphosphocholine of claim 1 or a pharmaceutically- acceptable salt thereof in the front of liposome.

* * * * *

UNITED STATES PATENT AND TRADEMARK OFFICE
CERTIFICATE OF CORRECTION

PATENT NO : 5,776,915
DATED : July 7, 1998
INVENTOR(S): Andrew C. Peterson and Haridasan K. Nair It is certified that error appears in the above-identified patent and that said Letters Patent is hereby corrected as shown below:

At column 7, line 23, delete "composition" and insert therefor --compositions comprising--.

In claim 19, line 2 (column 18, line 43), delete "front of" and insert therefor --form of a--.

Signed and Sealed this

Fifteenth Day of September, 1998

*Attest:*

BRUCE LEHMAN

*Attesting Officer*    Commissioner of Patents and Trademarks